(12) United States Patent
Shin et al.

(10) Patent No.: US 7,552,746 B2
(45) Date of Patent: Jun. 30, 2009

(54) FLUID CONTAINER APPARATUS HAVING SUPPORT ELEMENTS FOR SUPPORTING APPARATUS COMPONENTS

(75) Inventors: Michael Shin, Pleasanton, CA (US); Michael R. Lang, Pleasant Hill, CA (US); Francisco Magno, San Ramon, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 54 days.

(21) Appl. No.: 11/671,822

(22) Filed: Feb. 6, 2007

(65) Prior Publication Data
US 2007/0209712 A1    Sep. 13, 2007

Related U.S. Application Data

(63) Continuation of application No. PCT/US2005/027976, filed on Aug. 6, 2005.

(60) Provisional application No. 60/599,020, filed on Aug. 6, 2004.

(51) Int. Cl.
*B65B 1/30* (2006.01)
(52) U.S. Cl. .................................. 137/587; 137/377
(58) Field of Classification Search ............. 137/377, 137/376, 583, 587, 588, 343, 356, 382; 222/183; 165/81, 82
See application file for complete search history.

(56) References Cited

U.S. PATENT DOCUMENTS

| | | | |
|---|---|---|---|
| 1,326,277 A * | 12/1919 | Latourelle | 165/82 |
| 2,216,890 A | 10/1940 | Philipps | 225/26 |
| 2,832,366 A * | 4/1958 | Farison | 137/132 |
| 2,961,221 A * | 11/1960 | Friese et al. | 165/83 |
| 3,001,375 A | 9/1961 | Tauscher | 62/51 |
| 3,097,497 A | 7/1963 | Fitt et al. | 62/52 |
| 3,536,095 A | 10/1970 | Carteret et al. | 137/557 |
| 3,588,040 A | 6/1971 | Ward | 251/244 |
| 3,800,819 A * | 4/1974 | McKee | 137/343 |
| 4,181,126 A | 1/1980 | Hendry | 128/201.21 |
| 4,553,776 A | 11/1985 | Dodd | 285/212 |
| 4,718,452 A | 1/1988 | Maitland | 137/592 |
| 4,913,316 A * | 4/1990 | Richter | 222/1 |
| 5,169,029 A * | 12/1992 | Behar et al. | 222/1 |
| 5,299,709 A * | 4/1994 | Beerbower et al. | 137/356 |
| 5,558,139 A | 9/1996 | Snyder | 141/95 |
| 5,561,983 A | 10/1996 | Remes et al. | 62/48.1 |
| 5,878,744 A | 3/1999 | Pfeiffer | 128/204.23 |

(Continued)

FOREIGN PATENT DOCUMENTS

DE    1145650    3/1963

(Continued)

OTHER PUBLICATIONS

International Search Report (with Written Opinion), PCT/US2005/027976, 13 pages, mailed Feb. 21, 2006.

*Primary Examiner*—John Fox

(57) ABSTRACT

A fluid storage and delivery apparatus may include a fluid container, a first apparatus component, and a housing. One or more support members may be coupled to the housing and configured to secure the first apparatus component physically separate from the fluid container. The first apparatus component may be indirectly coupled to the fluid container by one or more coupling members at least partially defining a fluid passageway between the first apparatus component and the fluid container.

21 Claims, 14 Drawing Sheets

U.S. PATENT DOCUMENTS

| | | | |
|---|---|---|---|
| 6,176,255 B1 * | 1/2001 | Robinson | 137/377 |
| 6,209,749 B1 * | 4/2001 | Guess | 220/724 |
| 6,378,546 B1 * | 4/2002 | Hansen | 137/208 |
| 6,393,802 B1 * | 5/2002 | Bowser et al. | 53/403 |
| 6,393,846 B1 | 5/2002 | Frye | 62/50.5 |
| 6,418,962 B1 * | 7/2002 | Wozniak et al. | 137/266 |
| 6,427,690 B1 | 8/2002 | McCombs et al. | 128/204.26 |
| 6,446,845 B1 | 9/2002 | Steiger | 222/509 |
| 6,502,607 B2 | 1/2003 | Brown et al. | 141/1 |
| 6,637,469 B2 * | 10/2003 | Hoffman et al. | 141/8 |
| 6,732,759 B2 | 5/2004 | Romanek et al. | 137/588 |
| 6,742,517 B1 | 6/2004 | Frye et al. | 128/201.21 |
| 7,028,553 B2 * | 4/2006 | Smith et al. | 73/756 |
| 2003/0173376 A1 * | 9/2003 | Bilskie et al. | 222/129.1 |

FOREIGN PATENT DOCUMENTS

WO    WO 2006/017781 A2    2/2006

* cited by examiner

FLUID CONTAINER APPARATUS HAVING SUPPORT ELEMENTS FOR SUPPORTING APPARATUS COMPONENTS

RELATED APPLICATION

This application is a continuation of co-pending International Application No. PCT/US2005/027976 filed Aug. 6, 2005, which designates the United States, and claims priority to and the benefit of U.S. Provisional Application No. 60/599,020, filed Aug. 6, 2004, the contents of which are hereby incorporated by reference in their entirety.

TECHNICAL FIELD

The present disclosure is related generally to fluid container apparatuses, and more particularly to a fluid container apparatus having support elements for supporting, aligning, and/or securing apparatus components.

BACKGROUND

Therapeutic oxygen is commonly provided to subjects in order to treat a variety of medical conditions, including various conditions in which the subject suffers from a loss of lung capacity. Examples of medical conditions that may result in a loss of lung capacity include chronic obstructive pulmonary disease (COPD) such as asthma, emphysema, etc., as well as cystic fibrosis, lung cancer, lung injuries, and cardiovascular diseases. Pure or substantially pure oxygen may be delivered to the subject to treat the relevant condition. Inhaling the delivered therapeutic oxygen may help the subject achieve and/or maintain an adequate level of oxygen in his or her bloodstream.

Portable therapeutic oxygen has conventionally been provided in two ways. The first approach involves storing compressed oxygen gas in a pressure container and delivering the gas through a pressure regulator and through a hose, lumen, cannula or other passage to the subject's breathing orifices (e.g., nostrils). In some instances, the container may be wheeled such that the subject may be at least somewhat mobile. However, portable compressed gaseous oxygen systems suffer from various disadvantages, such as the fact that a full portable container typically lasts a relatively short period of time, and the fact that the system may be relatively heavy and obtrusive, which may limit the subject's mobility.

The second approach involves storing liquid oxygen (or "LOX") in a portable container and delivering gaseous oxygen evaporated from the liquid oxygen to the subject through a hose, lumen, cannula or other passage to the subject's breathing orifices (e.g., nostrils). Such an apparatus for storing liquid oxygen and/or delivering evaporated gaseous oxygen may be referred to as an "LOX apparatus." Although oxygen is typically a gas at standard atmospheric conditions, it may be maintained as a liquid at very low temperatures, which substantially reduces the volume of the oxygen, thus substantially reducing the required size of the LOX apparatus as compared to compressed gaseous oxygen systems. LOX apparatuses typically include a vacuum-insulated container or a partially vacuum-insulated container for storing and maintaining the LOX at a very low temperature.

As compared to compressed gaseous oxygen systems, an LOX apparatus enjoys a longer usable charge for a given size or weight. Accordingly, the LOX apparatus can be much smaller than known compressed gaseous oxygen systems and can provide the same or longer duration of useable charge, while being lighter and/or less obtrusive.

In order to fill, or "charge," the vacuum-insulated container of the LOX apparatus with LOX, the LOX apparatus may include a fill port in fluid communication with the container. The fill port may be configured to temporarily engage or connect to a LOX reservoir or some other source of LOX. The fill port may facilitate the transfer of LOX from the LOX reservoir to the container of the LOX apparatus. The fill port typically undergoes stress loading during filling due to the contact with the LOX reservoir and associated forces and/or pressures. To engage the fill port with the LOX reservoir, a user may need to apply pressure to the fill port to activate the connection.

The fill port of an LOX apparatus may be physically attached to the LOX container. For example, the fill port may be attached to the container by a flange that is mechanically fastened to the fill port (e.g., using a nut and screw) and mechanically fastened (e.g., using a worm-drive clamp) or welded to the container. This arrangement may transfer some or all of the physical stresses experienced by the fill port (e.g., during filling) from the fill port to the container. Whether the fill port is connected to the container via welding, braze, or mechanical fastener, the cyclical stress on the container may, especially over time, cause the vacuum shell or the container to be compromised or punctured. Similarly, the stresses transferred to the container may cause the container and its attached components to shift both horizontally, vertically and/or rotationally, which may cause undesirable load paths and/or stress points. These load paths and/or stress points may cause leakage within the LOX apparatus and/or failures of one or more of the LOX apparatus components. In addition, in situations in which flanges are welded to the container (for coupling one or more components to the container), the welding may cause a weld puncture and/or thin wall distortion resulting from overheating, which may weaken the container. Also, such flanges used for attaching components to the container may provide potential locations for leakage and/or freezing.

SUMMARY

In accordance with the present disclosure, fluid container apparatuses, and more particularly fluid container apparatuses having support elements for supporting, aligning, and/or securing apparatus components, may be provided.

In accordance with one embodiment of the present disclosure, a fluid storage and delivery apparatus includes a fluid container, a first apparatus component, and a housing. One or more support members may be coupled to the housing and configured to secure the first apparatus component physically separate from the fluid container. The first apparatus component may be indirectly coupled to the fluid container by one or more coupling members at least partially defining a fluid passageway between the first apparatus component and the fluid container.

In accordance with another embodiment of the present disclosure, a housing for a fluid storage and delivery apparatus includes a housing portion configured to at least partially house one or more components of the fluid storage and delivery apparatus. The housing also includes one or more support members coupled to the housing portion and configured to secure a first one of the components physically separate from a second one of the components. The first and second components may be indirectly coupled to each other by one or more coupling members at least partially defining a fluid passageway between the first and second components.

In accordance with yet another embodiment of the present disclosure, a fluid storage and delivery apparatus includes means for storing a fluid, means for communicating at least a portion of the fluid to or from the fluid storage means, means for at least partially housing the fluid storage means and the fluid communication means, and means coupled to the housing for securing the fluid communication means physically separate from the fluid storage means. The fluid communication means may be indirectly coupled to the fluid storage means by one or more coupling members at least partially defining a fluid

BRIEF DESCRIPTION OF THE DRAWINGS

Some embodiments of the disclosure may be understood by referring, in part, to the following description and the accompanying drawings, in which like reference numbers refer to the same or like parts, and wherein.

DETAILED DESCRIPTION

Selected embodiments of the disclosure may be understood by reference, in part, to FIGS. 1-23, wherein like number refer to same and like parts.

Figure 1:
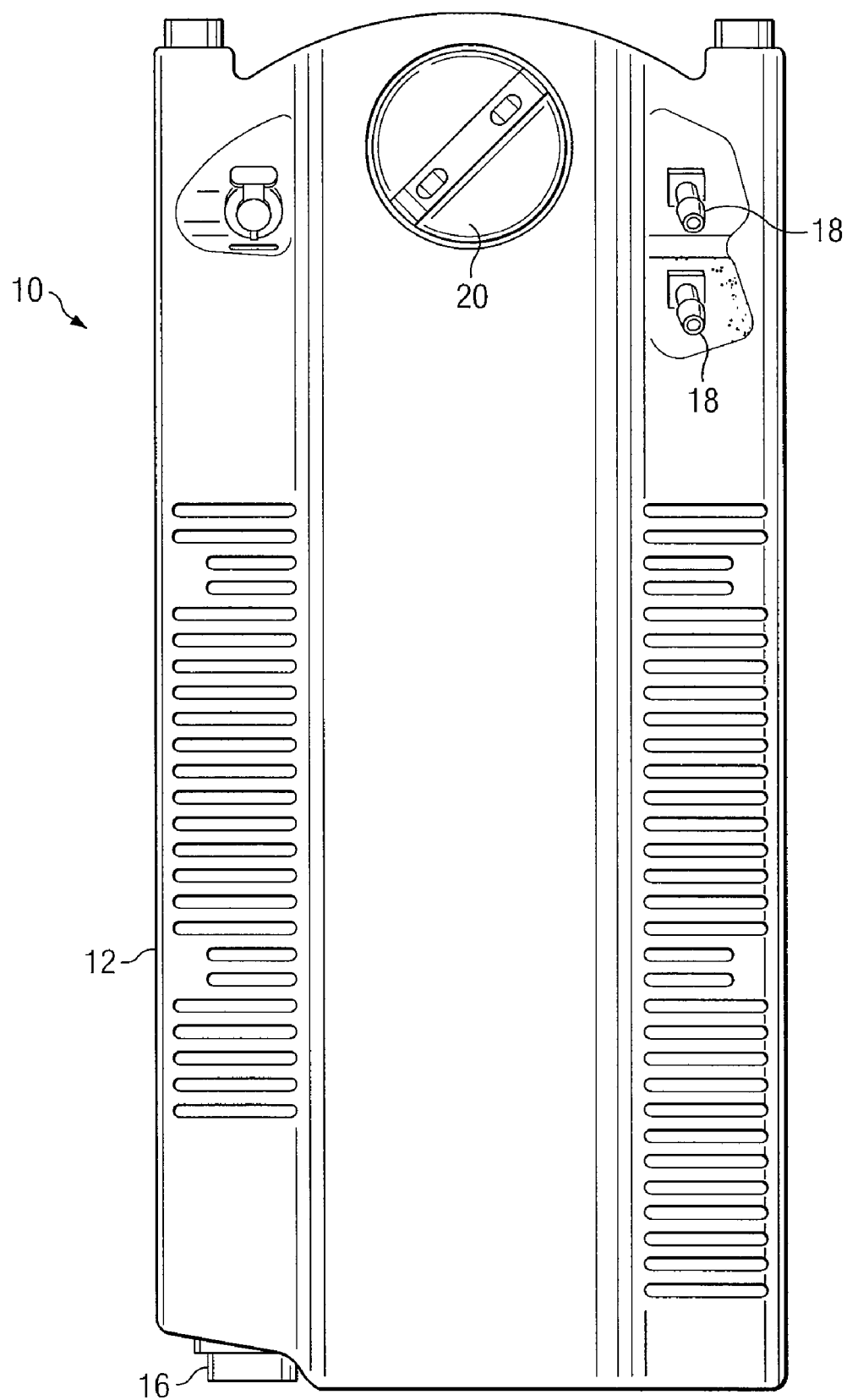
FIG. 1 illustrates a fluid management apparatus according to one embodiment of the present disclosure.

FIG. 1 illustrates a fluid management apparatus 10 according to one embodiment of the present disclosure. Fluid management apparatus 10 may be generally operable to provide and/or control the storage and/or delivery of one or more fluids, such as gasses and/or liquids, for example. In some embodiments, fluid management apparatus 10 may comprise a portable liquid oxygen (LOX) apparatus generally operable to store liquid oxygen and deliver gaseous oxygen (e.g., evaporated from the liquid oxygen) to a subject via one or more suitable gas passageways. The following discussion focuses on such LOX apparatuses 10. However, it should be understood that in other embodiments, apparatus 10 may or not be portable, and may be used for storing and/or delivering any other fluid or fluids (instead of, or in addition to, oxygen).

Figure 2:
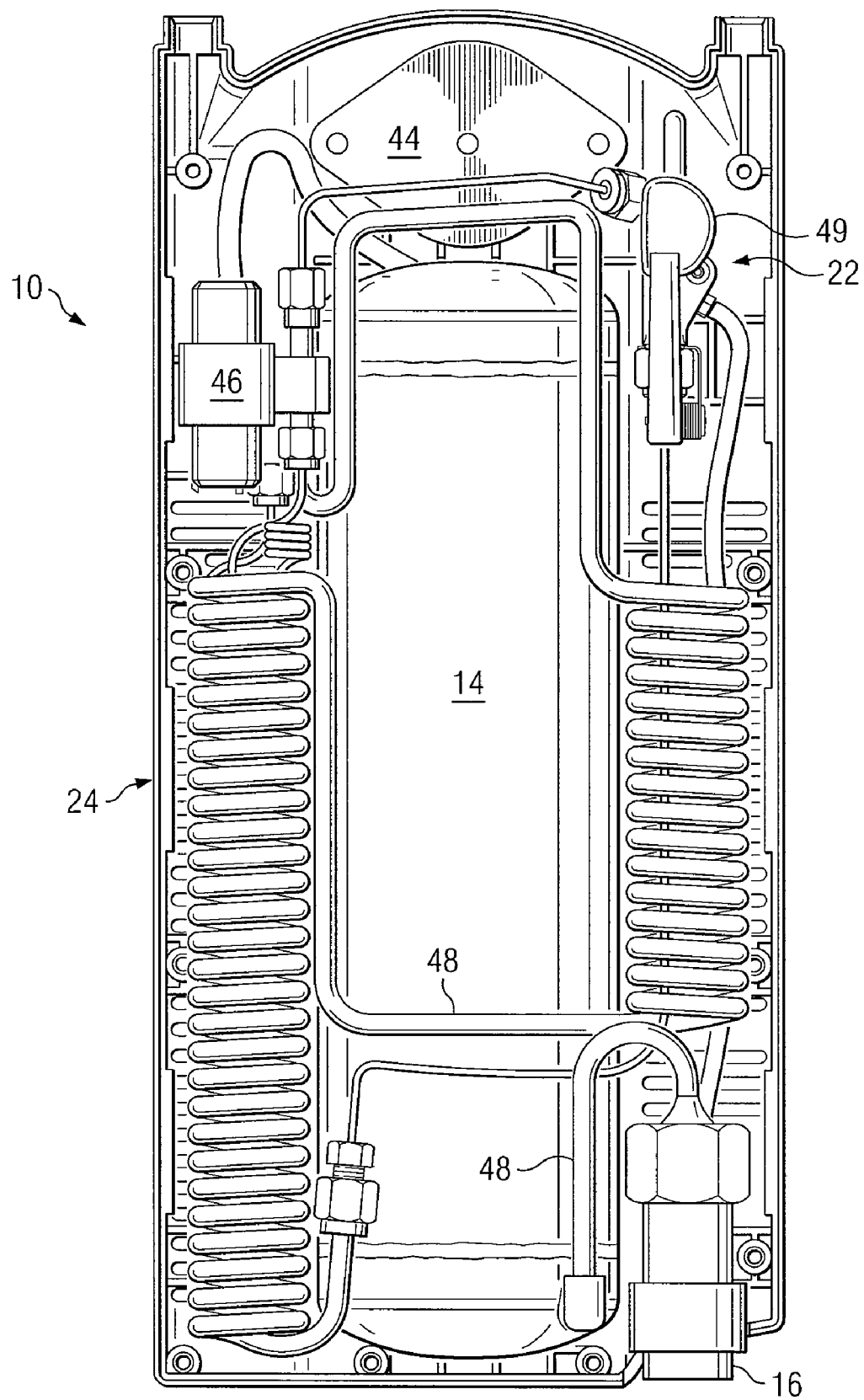
FIG. 2 illustrates an example LOX apparatus having the rear housing removed to show various components of the LOX apparatus housed within front housing.

The example LOX apparatus 10 shown in FIG. 1 may include a housing 12, a container 14 (see, e.g., FIG. 2), a fill port 16, one or more outlets 18, a control device 20, and a vent valve 22 (see, e.g., FIG. 2). Housing 12 may be configured to fully or partially house various components of apparatus 10, such as container 14, fill port 16, vent valve 22, outlets 18, and/or control device 20, for example. Housing 12 may include multiple portions that are coupled together in any suitable manner to form a housing around components of apparatus 10. For example, housing 12 may include a front housing 24 and a rear housing 26 (see, e.g., FIGS. 3 and 4) that couple together to form a shell or housing around components of apparatus 10. In addition, in some embodiments, housing 12 may include support members 30 (see, e.g., FIGS. 3-11) coupled to and/or formed on the inside of front housing 24 and/or rear housing 26, which support members 30 may be generally configured to support, align, and/or secure one or more components of apparatus 10 in proper position.

Container 14 may be configured to receive, store, and/or deliver oxygen. Fill port 16 may be in fluid communication with container 14 and may be configured for filling container 14 with liquid oxygen, which filling may be referred to as "charging" container 14. For example, fill port 16 may be configured to temporarily engage or connect to a LOX reservoir or some other source of LOX and facilitate the transfer of LOX from the LOX reservoir to container 14.

Outlets 18 may be in fluid communication with container 14 and may be configured for delivering gaseous oxygen evaporated from the liquid oxygen in container 14 to a subject. For example, each outlet 18 may be configured to be attached to a hose, lumen, cannula or other passageway that may deliver the gaseous oxygen to the subject's breathing orifice(s) (e.g., nostrils).

Control device 20 may be configured for adjusting or controlling the operation of apparatus 10. In some embodiments, control device 20 is configured to be manipulated by a user to adjust or control the operation of apparatus 10. For example, control device 20 may include one or more knobs, dials, switches, buttons, or any other type of manipulatable devices. In certain embodiments, control device 20 may include a single device (e.g., a single dial, knob or switch) that allows a user to select from (a) multiple modes of oxygen flow and/or (b) multiple volumetric flow rates for the gaseous oxygen delivered by apparatus 10. Example modes of oxygen flow may include (a) continuous mode and/or (b) conserve (or "demand") mode. Continuous mode may provide a steady, continuous flow of oxygen. Conserve mode may provide a regulated flow of oxygen, which may be regulated based on various inputs, such as physiological inputs from the subject. For example, in the conserve mode, the delivered oxygen flow may be reduced or interrupted during exhalation, which may reduce the amount of oxygen wasted during exhalation. In some embodiments, multiple different conserve modes may be provided, which may differ based on various parameters, such parameters regarding the detection of the subject's inhalation or attempted inhalation, for example. In certain embodiments, control device 20 may include a single device that allows a user to select both (a) between continuous mode and conserve mode and (b) the intensity or flow rate for the selected mode or a particular type or level of continuous or conserve mode.

FIG. 2 illustrates an apparatus 10 having the rear housing 26 removed to show various components of apparatus 10 housed within front housing 24, according to one embodiment of the disclosure. For example, container 14, fill port 16, vent valve 22, a regulator 44, a relief/economizer valve 46, and tubing 48 are indicated in FIG. 2.

Vent valve 22 may allow a user to vent oxygen from container 14, such as during the filling of container 14 or otherwise. Vent valve 22 may include a vent valve lever 49, which may be actuated in order to open a valve allowing oxygen (liquid and/or gas) to vent from container 14. For example, vent valve lever 49 may be actuated during the filling of container 14 to vent gaseous oxygen in order to release pressure in container 14, thus allowing container 14 to be filled with LOX. In addition, the user may also identify when the container 14 is full of LOX when LOX begins exiting through vent valve 22.

Regulator 44 may be generally operable to control the flow of gaseous oxygen being delivered by apparatus 10, and may be controlled or adjusted by control device 20 or otherwise controlled or adjusted. For example, regulator 44 may be operable to control (a) the flow rate and/or (b) the mode of operation or gas delivery for the gaseous oxygen delivered by apparatus 10. In some embodiments, regulator 44 may be operable to provide multiple modes of operation or gas delivery, such as (a) continuous mode and/or (b) conserve or demand mode, such as described above regarding control device 20. In addition, regulator 44 may be able to provide multiple intensities, levels or settings for each of such operation or gas delivery modes. To provide such various options, in some embodiments, regulator 44 may include one or more valves, apertures of various shapes and/or sizes, and/or any other suitable components.

Relief/economizer valve 46 may be generally operable to regulate the pressure of oxygen within container 14. For example, valve 46 may open to allow oxygen gas from a gaseous head-space in container 14 to pass through when the pressure of the oxygen gas in container 14 exceeds a predetermined threshold level, and may otherwise remain closed allowing oxygen gas from evaporated LOX to pass through.

It should be understood that apparatus 10 may also include any other components suitable for use in an LOX apparatus. For example, apparatus 10 may also include a heat exchanger, for example.

As discussed above, one or more components of apparatus 10 may be supported, aligned, and/or secured within housing 12 by one or more support members 30 coupled to or integrated with housing 12. For example, one or more of container 14, fill port 16, vent valve 22, regulator 44, and/or relief/economizer valve 46 may be supported, aligned, and/or secured by one or more support members 30 coupled to or integrated with front housing 24 and/or rear housing 26.

Figure 3:
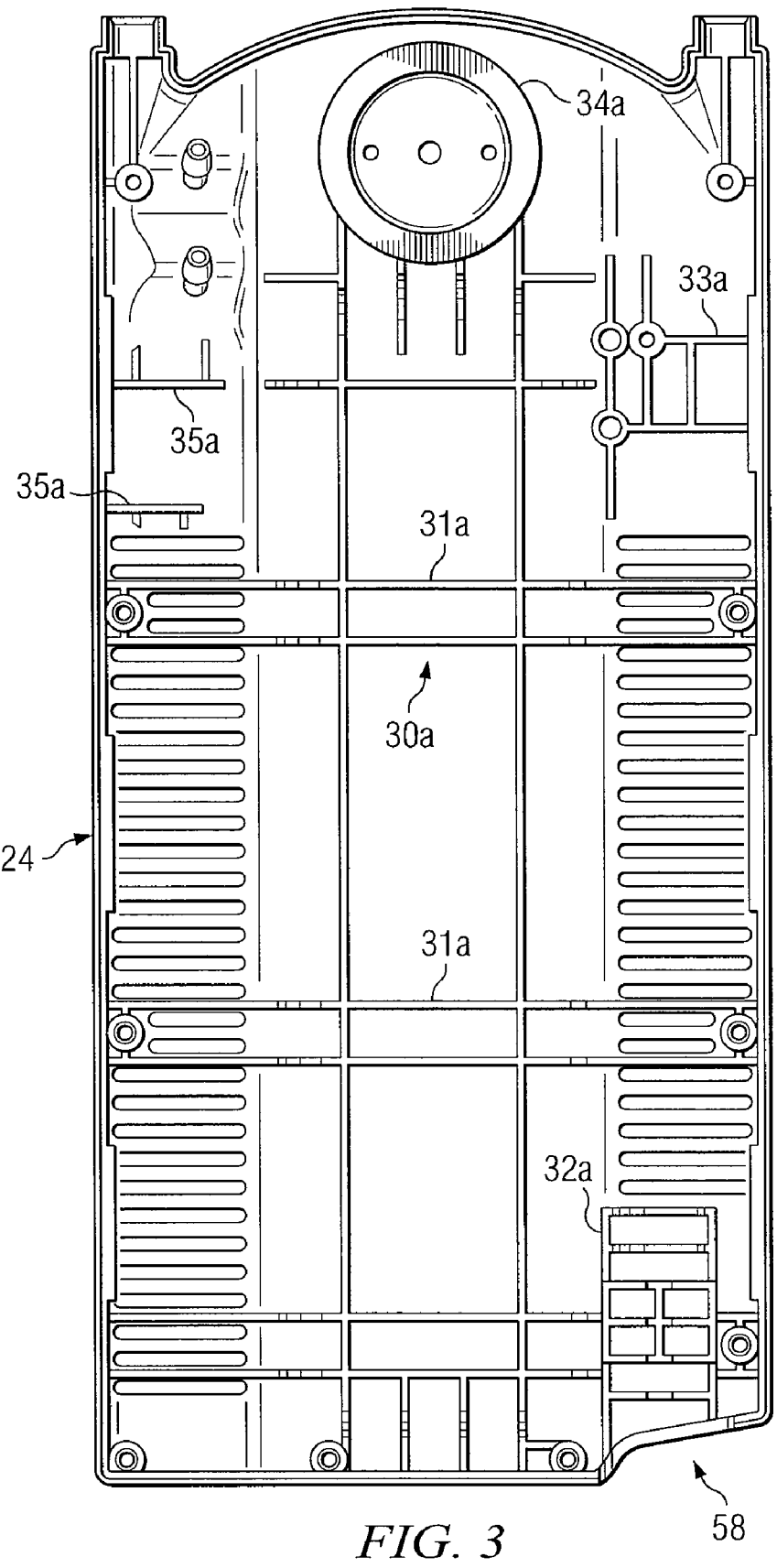
FIG. 3 illustrates the inside of the front housing of an example LOX apparatus according to one embodiment of the disclosure.
Figure 4:
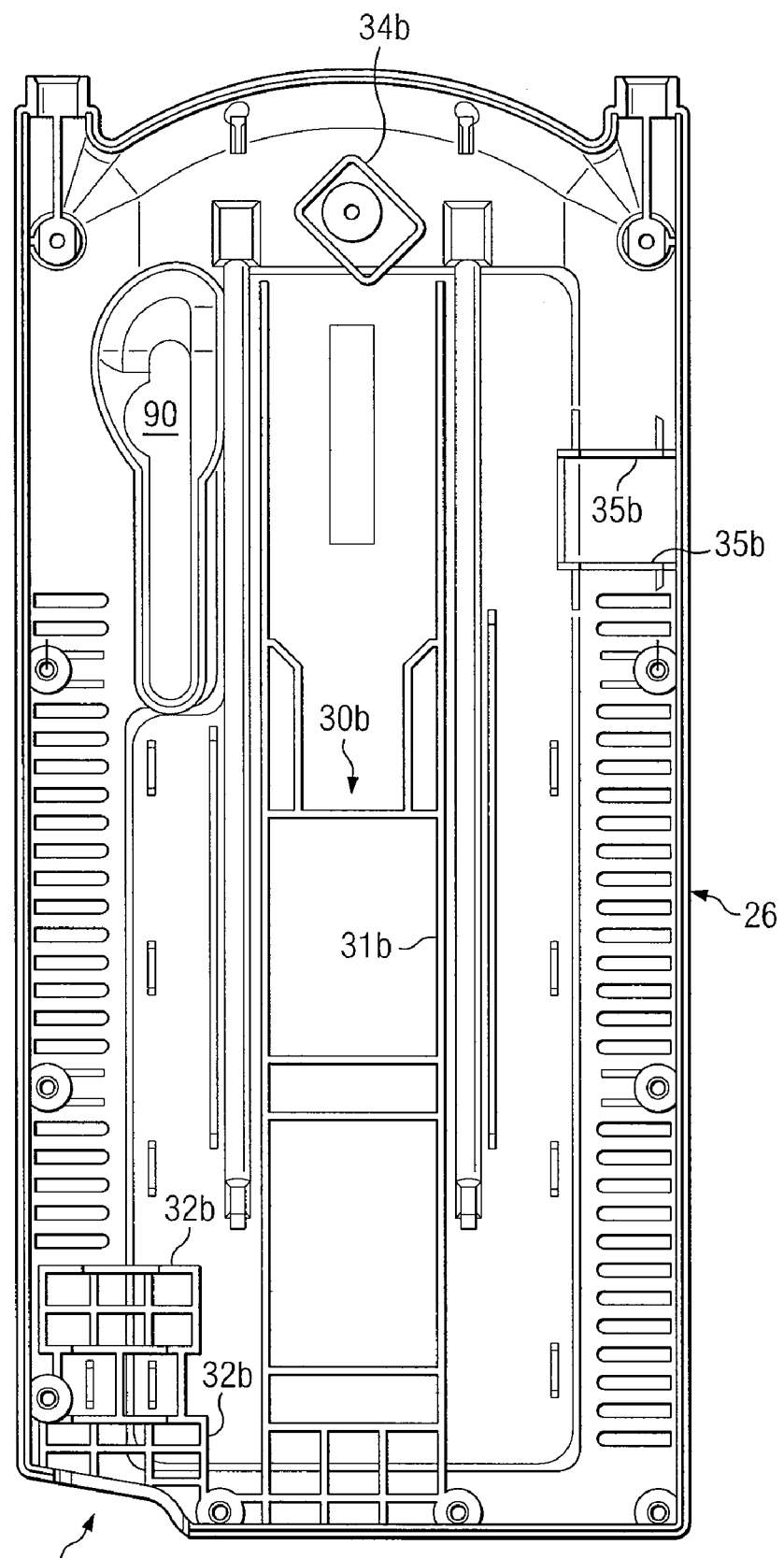
FIG. 4 illustrates the inside of the rear housing of an example LOX apparatus according to one embodiment of the disclosure.

For example, as shown in FIGS. 3 and 4, container 14 may be supported, aligned, and/or secured in place by one or more container support members 31; fill port 16 may be supported, aligned, and/or secured in place by one or more fill port support members 32; vent valve 22 may be supported, aligned, and/or secured in place by one or more vent valve support members 33; regulator 44 may be supported, aligned, and/or secured in place by one or more regulator support members 35; and relief/economizer valve 46 may be supported, aligned, and/or secured in place by one or more relief/economizer valve support members 36.

One, some or all of support members 30 may include one or more front support members 30a coupled to or integrated with front housing 24 and/or one or more rear support members 30b coupled to or integrated with rear housing 26, as shown and discussed below with respect to FIGS. 3 and 4. In some embodiments, one or more front support members 30a may be configured to cooperate with one or more corresponding rear support members 30b to support, align, and/or secure one or more components in place. For example, front support members 30a may cooperate with rear support members 30b to provide support to one or more components of apparatus 10 such that forces acting upon such components do not damage such components or other components of apparatus 10, whether during the filling of container 14, during the operation of apparatus 10, or otherwise.

Support members 30 may include any members or elements configured to help support, align, and/or secure a component in place. Support members 30 may have any shape, size, and orientation. For example, one or more generally straight support members 30 may be oriented horizontally, vertically, or at any other angle in any dimension. In some embodiments, one or more support members 30 may comprise ribs, brackets, clips, or may have any other shape or configuration. As discussed above, support members 30 may be coupled to or integrated with housing 12 in any suitable manner. For example, in some embodiments, one or more support members 30 may be formed integrally with housing 12 (e.g., front housing 24 and/or rear housing 26), such as by molding or casting, for example. In other embodiments, one or more support members 30 may be coupled to housing 12 (e.g., front housing 24 and/or rear housing 26) in any suitable manner, such as by adhesive, weld, braze, clipping, snapping, or using one or more mechanical fasteners, for example. In addition, support members 30 may be formed from any suitable material, such as plastic, metal, or composite, for example.

In some embodiments, the support members 30 for housing particular components may include multiple portions having different shapes, sizes or contours configured to receive different portions of such particular components. One or more support members 30 may be shaped, sized, and/or contoured to correspond with the shape, size, and/or contours of the corresponding component(s) of apparatus 10. For example, as discussed below with reference to FIG. 5, fill port support members 32 may include multiple portions having different shapes and/or contours configured to receive the different shapes and/or contours of different portions or components of fill port 16.

FIG. 3 illustrates the inside of a front housing 24 of an example LOX apparatus 10, according to one embodiment of the disclosure. As discussed above, apparatus 10 may include one or more front support members 30a coupled to or integrated with front housing 24. In this embodiment, front support members 30a may include container support members 31a, fill port support members 32a, vent valve support members 33a, regulator support members 34a, and/or relief/economizer valve support members 35a.

FIG. 4 illustrates the inside of a rear housing 26 of an example LOX apparatus 10, according to one embodiment of the disclosure. As discussed above, apparatus 10 may include one or more rear support members 30b coupled to or integrated with rear housing 26. In this embodiment, rear support members 30b may include container support members 31b, fill port support members 32b, regulator support members 34b, and/or relief/economizer valve support members 35b.

Container support members 31a and 31b may be configured to cooperate to support, align, and/or secure container 14 in place; fill port support members 32a and 32b may be configured to cooperate to support, align, and/or secure fill port 16 in place; vent valve support members 33a may be configured to support, align, and/or secure vent valve 22 in place, regulator support members 34a and 34b may be configured to cooperate to support, align, and/or secure regulator 44 in place, and relief/economizer valve support members 35a and 35b may be configured to cooperate to support, align, and/or secure relief/economizer valve 46 in place.

Figure 9:
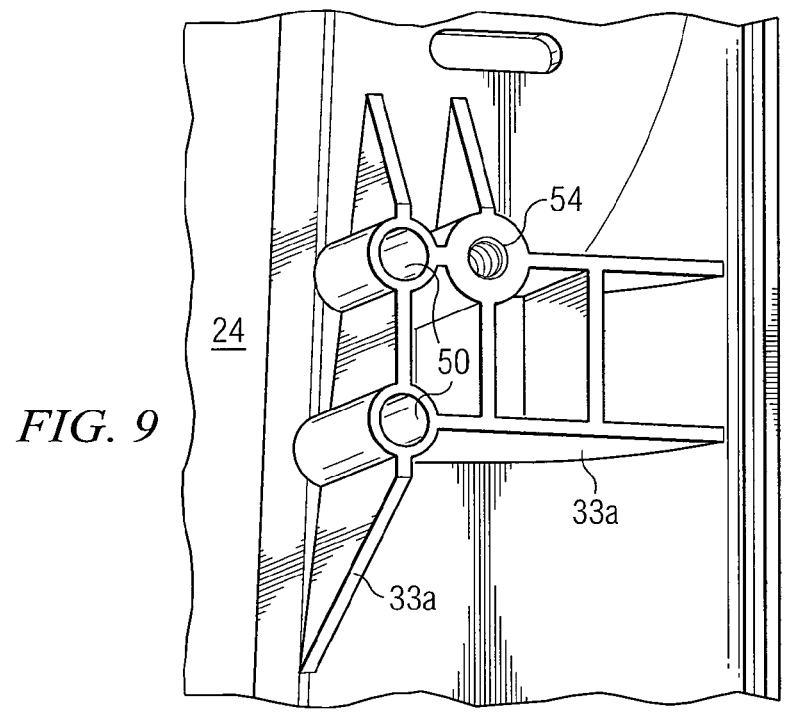
FIG. 9 illustrates example vent valve support members coupled to or formed in a front housing of an LOX apparatus, according to one embodiment of the disclosure.

One or more support members 30a and/or 30b may be shaped and/or sized to mate with or receive the corresponding component(s) of apparatus 10. For example, as shown in FIG. 3 (and more clearly shown in FIG. 5), particular fill port support members 32a may be V-shaped to receive a V-shaped portion of fill port 16. As another example, as shown in FIG. 9 and discussed below, vent valve support members 33a may include tubular openings 50 shaped, sized, and/or aligned to receive alignment pegs 52 (shown in FIGS. 17-19) extending from vent valve 22 in order to properly align vent valve 22 relative to front support members 33a. In addition, one or more support members 30a and/or 30b may be configured to receive mechanical fasteners, such as screws, bolts, or clips, for example. For instance, as shown in FIG. 3, vent valve support members 33a may form a screw hole 54 configured to receive a screw 56 (see FIG. 10) for securing vent valve 22 to front housing 24.

Some or all of support members 30a and/or 30b may provide one, some or all of the following functions or advantages. First, one or more of support members 30a and/or 30b may support, align, and/or secure particular components within housing 12 as desired. This may ensure the proper alignment of particular components and/or increase the overall stability and strength of apparatus 10. Second, one or more of support members 30a and/or 30b may physically decouple particular components of apparatus 10 from each other. For example, as shown in FIG. 2, one or more of support members 30a and/or 30b may be configured to physically decouple fill port 16, vent valve 22, regulator 44, relief/economizer valve 46, and/or any other component from container 14, such that one or more of such components are not directly coupled to container 14. Thus, for example, as shown in FIG. 2, one or more of such components may be coupled to container 14 via tubing rather than being directly coupled to container 14, such as by a weld, braze, flange, or mechanical fastener (e.g., a worm-drive clamp or nut-and-bolt).

Physically decoupling components (e.g., fill port 16, vent valve 22, regulator 44, and/or relief/economizer valve 46) from container 14 may provide one or more advantages. For example, physically decoupling a component from container 14 may reduce or substantially eliminate the extent to which such stresses and strains experienced by that component (e.g., during filling of container 14, during operation of apparatus 10, or otherwise) are transferred to container 14, which may reduce the likelihood of container 14 being undesirably stressed or strained, or being punctured, cracked, or otherwise damaged.

In addition, securing components in place using support members 30 may reduce the extent to which such components may move (e.g., laterally in one or more directions and/or rotationally) relative to each other (e.g., relative to container 14), which may also reduce or substantially eliminate the extent to which such stresses and strains experienced by various components are transferred to each other (e.g., to container 14). Thus, the likelihood of stresses and strains on one component being undesirably transferred to another component (e.g., to container 14) may be reduced or substantially eliminated.

In addition, in some embodiments, physically decoupling components from each other using support members 30 may reduce or substantially eliminate damage caused to heat-sensitive components from high-temperature manufacturing techniques, such as welding or brazing, for example. Heat generated by such high-temperature manufacturing techniques may thus be localized, which may reduce the likelihood of heat-sensitive components physically decoupled from the area of a high-temperature process being damaged during such process.

The location of fill port support members 32a and/or 32b may ensure that fill port 16 is properly aligned with an opening 58 in front housing 24 and rear housing 26 (see FIGS. 3 and 4) such that a user may properly fill container 14 with LOX. Additionally, when front housing 24 and rear housing 26 are coupled, fill port front support members 32a may engages fill port rear support members 32b to provide a complete or near-complete 360-degree range of structural support for fill port 16. Such structural support may be particularly useful when fill port 16 is engaged with an external source of LOX, such as during the filling of container 14. During the filling of container 14, fill port 16 may experience various stresses and strains. As discussed above, decoupling fill port 16 from container 14 using support members 32a and/or 32b may reduce or substantially eliminate the extent to which such stresses and strains experienced by fill port 16 (whether associated with filling container 14 or otherwise) are transferred to container 14. In addition, securing fill port 16 in place using fill port support members 32a and/or 32b may reduce the extent to which fill port 16 may move (e.g., laterally in one or more directions and/or rotationally) relative to container 14, which may also reduce or substantially eliminate the extent to which such stresses and strains experienced by fill port 16 are transferred to container 14. Thus, the likelihood of stresses and strains on fill port 16 causing fill port 16 to break away from or puncture container 14, or otherwise form cracks or leaks in apparatus 10, may be reduced or substantially eliminated.

Vent valve support members 33a may be configured to receive the contours of vent valve 22 to properly align, support, and/or secure vent valve 22. As discussed above, vent valve support members 33a may incorporate a mechanical connection to help secure vent valve 22 to front housing 24, e.g., a screw, bolt, or other fastener, for example. In other embodiments, one or more vent valve support members 33 may be coupled to or integrated with rear housing 26, and may cooperate with vent valve support members 33a coupled to or integrated with front housing 24 in order to support, align, and/or secure vent valve 22.

As discussed above, container support members 31a and/or 31b coupled to and/or integrated with front housing 24 and/or rear housing 26 may support, align and/or secure container 14. This may reduce movement of container 14 (e.g., laterally in one or more directions and/or rotationally), which may in turn reduce vibrational noise.

Figure 5:
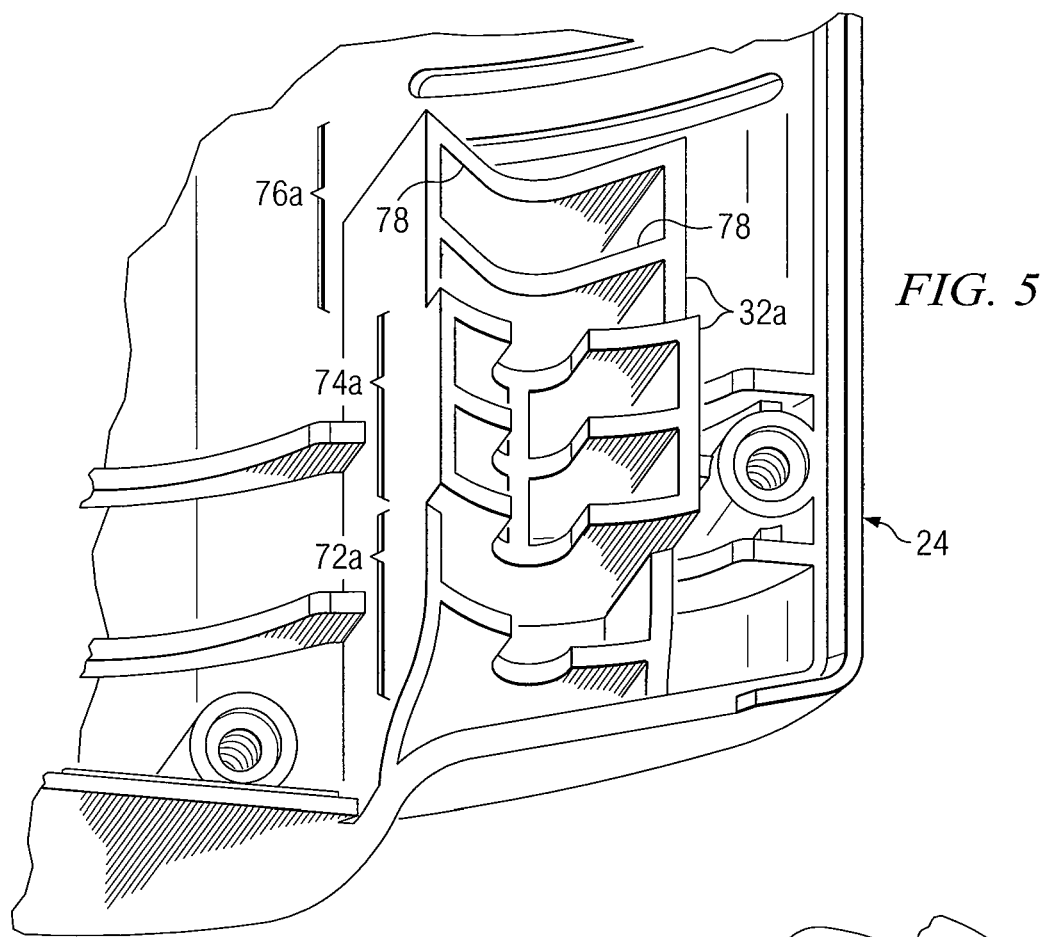
FIG. 5 illustrates example fill port support members coupled to or formed in a front housing of an LOX apparatus, according to one embodiment of the disclosure.

FIG. 5 illustrates example fill port support members 32a coupled to or formed in front housing 24 of apparatus 10, according to one embodiment of the disclosure. In some embodiments, fill port support members 32a may include multiple portions 72a, 74a, and 76a having different shapes and/or contours configured to receive the different shapes and/or contours of different portions or components of fill port 16. In this example embodiment, portion 76a may include generally V-shaped ribs 78 configured to receive a V-shaped portion of fill port 16.

Figure 6:
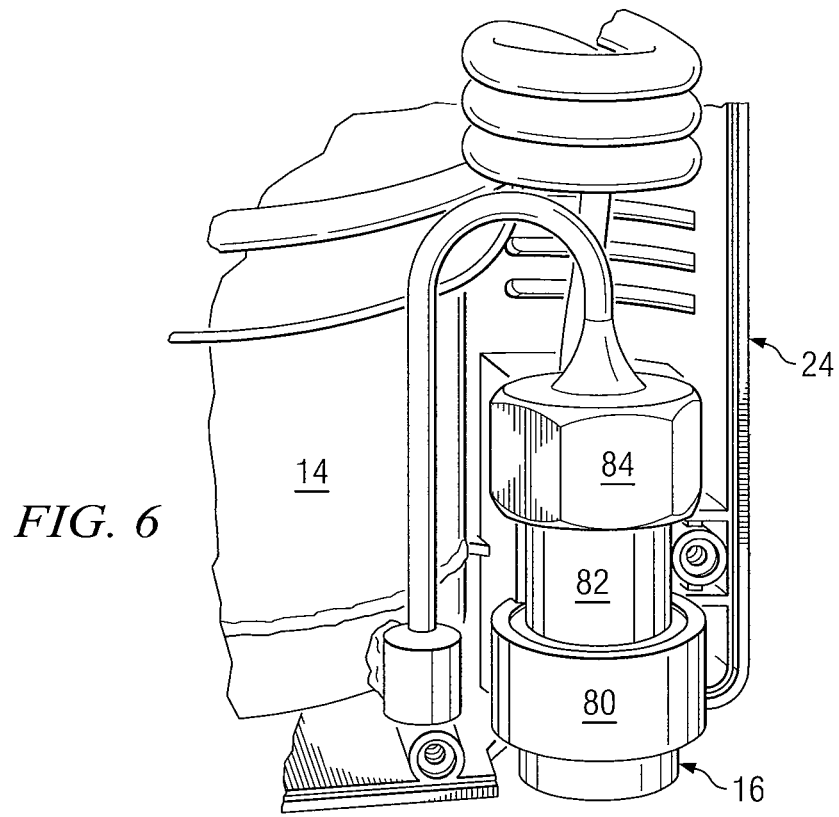
FIG. 6 illustrates an example fill port secured within the fill port support members shown in FIG. 5, according to one embodiment of the disclosure.

FIG. 6 illustrates an example fill port 16 secured within fill port support members 32a shown in FIG. 5, according to one embodiment of the disclosure. Different shaped and/or contoured portions 80, 82, and 84 of fill port 16 may be received within portions 72a, 74a, and 76a of fill port support members 32a (shown in FIG. 5).

Figure 7:
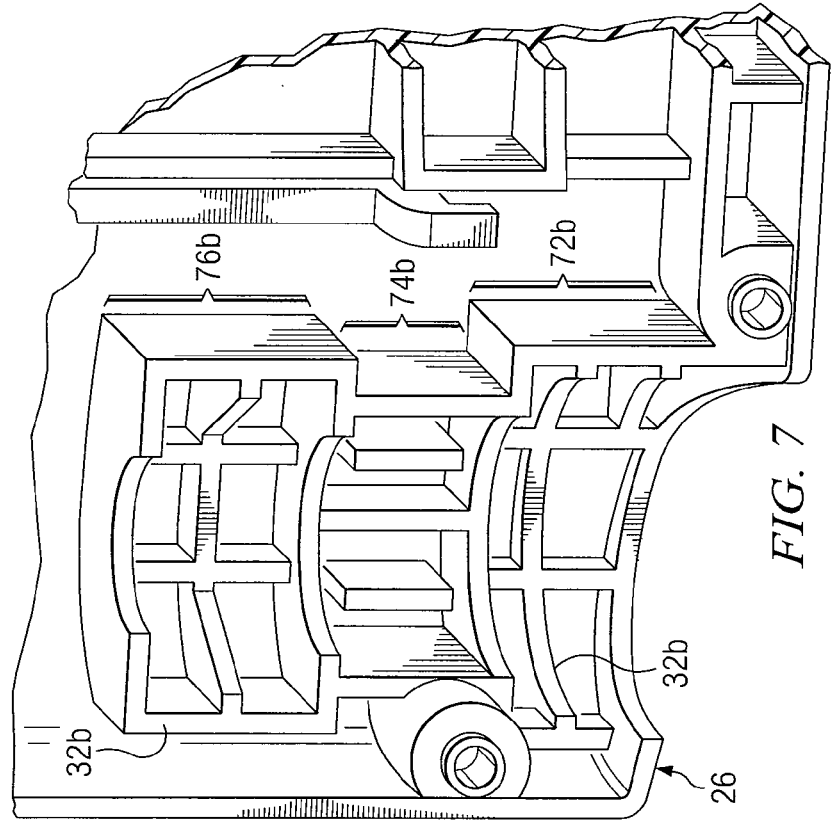
FIG. 7 illustrates example fill port support members coupled to or formed in a rear housing of an LOX apparatus, according to one embodiment of the disclosure.

FIG. 7 illustrates example fill port support members 32b coupled to or formed in rear housing 26 of apparatus 10, according to one embodiment of the disclosure. As discussed above, fill port support members 32b may cooperate with fill port support members 32a formed in front housing 24 in order to secure fill port 16 in position. Like fill port support members 32a, fill port support members 32b may include multiple portions 72b, 74b, and 76b having different shapes and/or contours configured to receive the different shapes and/or contours of different portions or components of fill port 16.

Figure 8:
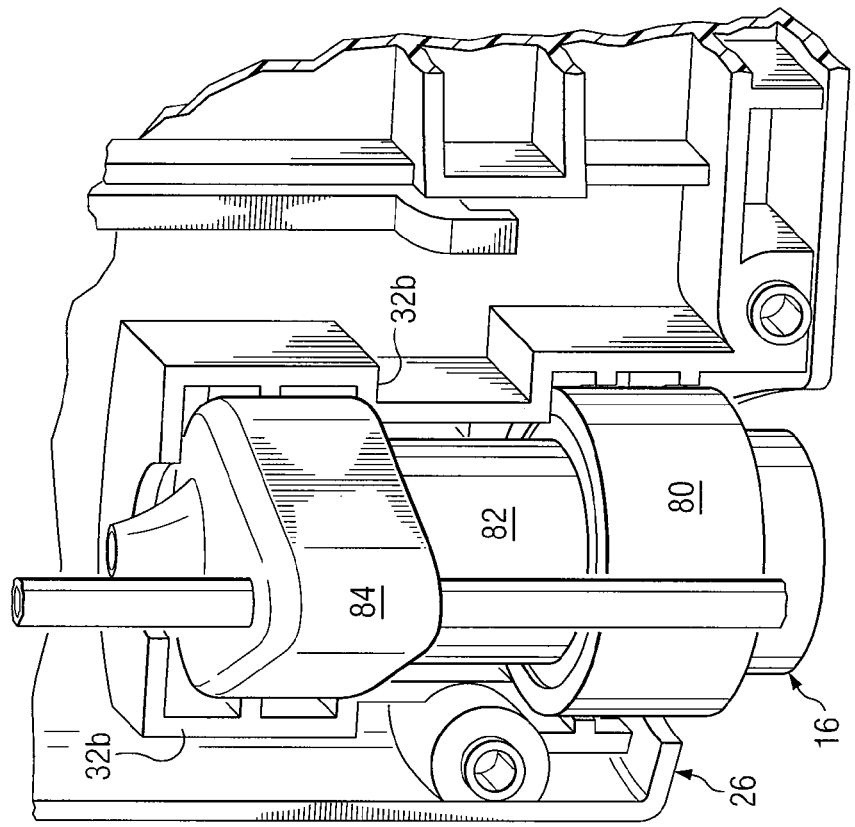
FIG. 8 illustrates an example fill port secured within the fill port support members shown in FIG. 7, according to one embodiment of the disclosure.

FIG. 8 illustrates an example fill port 16 secured within fill port support members 32b shown in FIG. 7, according to one embodiment of the disclosure. Other components of apparatus 10, such as container 14, have been removed for illustrative purposes. Different shaped and/or contoured portions 80, 82, and 84 may be received within portions 72b, 74b, and 76b of fill port support members 32b (shown in FIG. 7).

FIG. 9 illustrates example vent valve support members 33a coupled to or formed in front housing 24 of apparatus 10, according to one embodiment of the disclosure. As discussed above, in some embodiments, vent valve support members 33a may include one or more tubular openings 50 shaped, sized, and/or aligned to receive alignment pegs 52 (see FIGS. 17-19) extending from vent valve 22 in order to properly align vent valve 22 relative to front support members 33a. In addition, vent valve support members 33a may form a screw hole 54 configured to receive a screw 56 to secure vent valve 22 in place.

Figure 10:
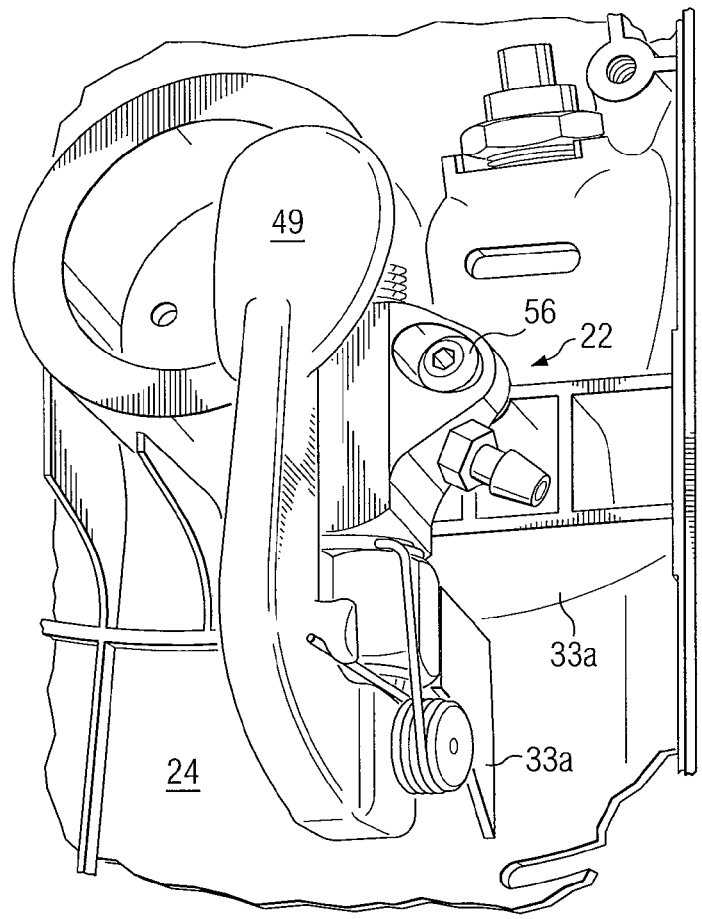
FIG. 10 illustrates an example vent valve secured by vent valve support members formed in a front housing of an LOX apparatus, according to one embodiment of the disclosure.

FIG. 10 illustrates an example vent valve 22 secured by vent valve support members 33a formed in front housing 24, according to one embodiment of the disclosure. Other components of apparatus 10, such as container 14, have been removed for illustrative purposes only. Pegs 52 extending from vent valve 22 may be positioned in openings 50, and a screw 56 may be screwed into screw hole 54 to secure vent valve 22. Vent valve lever 49 may extend through a lever opening 90 formed in rear housing 26 such that lever 49 may be easily accessed by a user.

Figure 11:
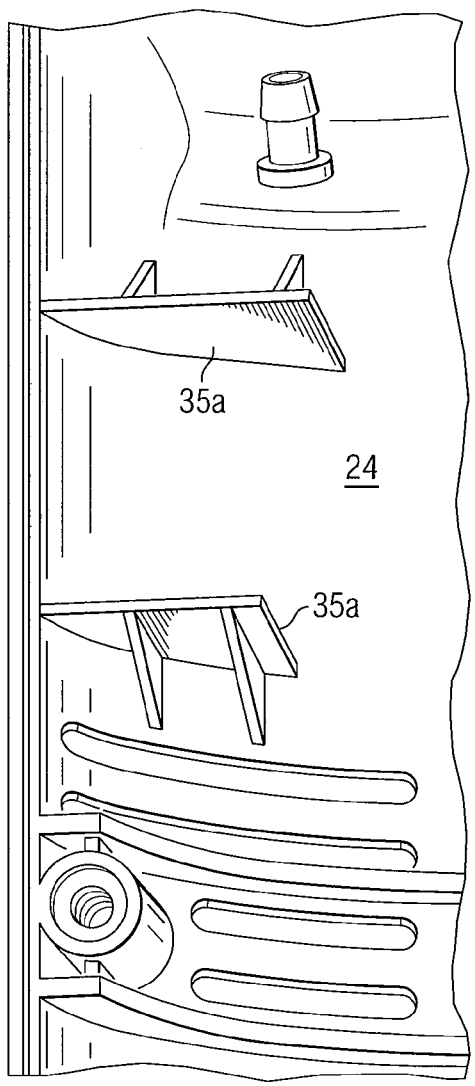
FIG. 11 illustrates example relief/economizer valve support members coupled to or formed in a front housing of an LOX apparatus, according to one embodiment of the disclosure.

FIG. 11 illustrates example relief/economizer valve support members 35a coupled to or formed in front housing 24 of apparatus 10, according to one embodiment of the disclosure. Relief/economizer valve support members 35a may cooperate with relief/economizer valve support members 35b coupled to or formed in rear housing 26 to support, align, and or secure relief/economizer valve 46 in position.

As discussed above, one or more of support members 30a and/or 30b may physically decouple particular components of apparatus 10 from each other, which may provide various advantages, such as decreasing the likelihood of container 14 becoming cracked or punctured due to various stresses and strains, for example. As discussed below, FIGS. 12-14 illustrate such decoupling of fill port 16, vent valve 22, and relief/economizer valve 46 from container 14.

Figure 12:
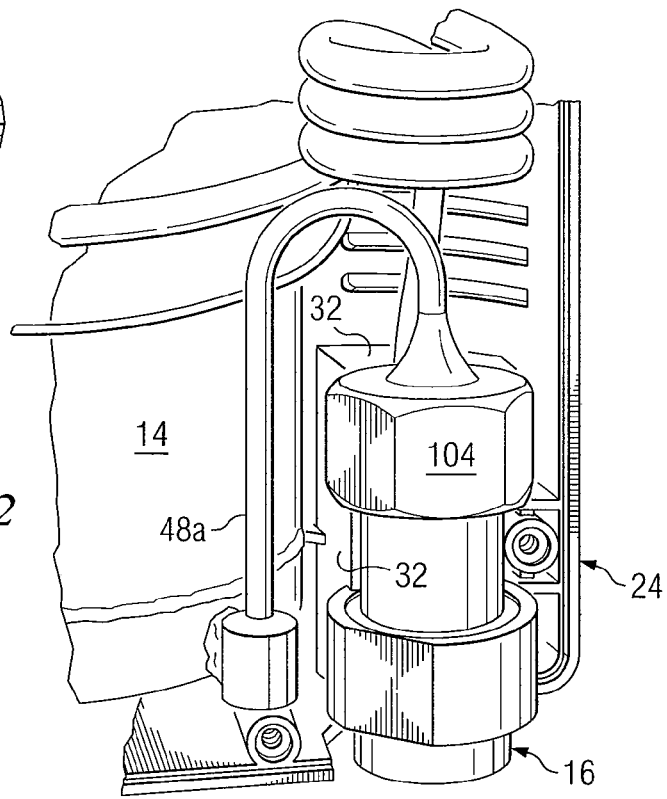
FIG. 12 illustrates an example fill port physically decoupled from a container in accordance with one embodiment of the disclosure.

FIG. 12 illustrates fill port 16 physically decoupled from container 14 in accordance with one embodiment of the disclosure. In this embodiment, fill port support members 32 secure fill port 16 physically separate from container 14, and fill port 16 is connected to container 14 by tubing 48a. Tubing 48a may be coupled to an adaptor 102 of fill port 16 and/or to container 14 in any suitable manner, such as by weld, braze, or mechanical fastener, for example. The shape and/or configuration of tubing 48a may provide some flexibility and/or dampening such that the transfer of stresses or strains from fill port 16 to container 14 may be reduced or substantially eliminated, as compared to a configuration in which fill port 16 is directly coupled to container 14.

Decoupling fill port 16 from container 14 may be advantageous, for example, when fill port 16 is engaged with an external source of LOX, such as during the filling of container 14. As discussed above, decoupling fill port 16 from container 14 using support members 32 may reduce or substantially eliminate the extent to which such stresses and strains experienced by fill port 16 (whether associated with filling container 14 or otherwise) are transferred to container 14. Thus, the likelihood of stresses and strains on fill port 16 causing fill port 16 to break away from or puncture container 14, or otherwise form cracks or leaks in apparatus 10, may be reduced or substantially eliminated.

Figure 13:
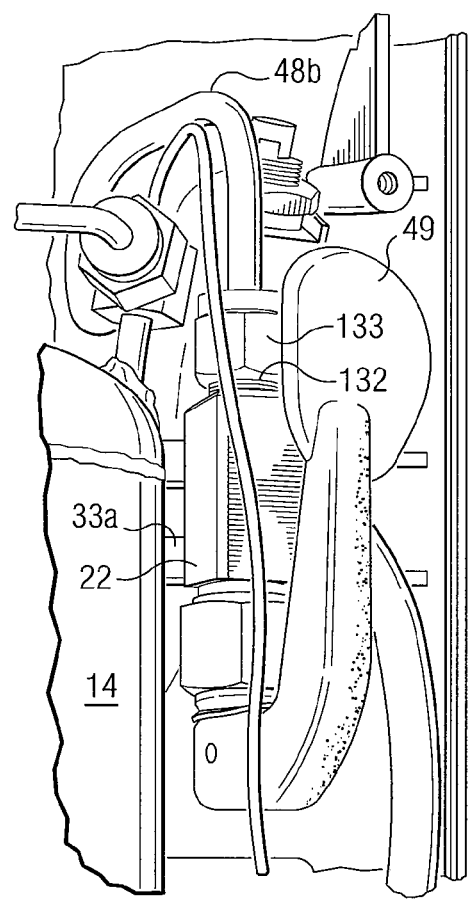
FIG. 13 illustrates an example vent valve physically decoupled from a container in accordance with one embodiment of the disclosure.
Figure 14:
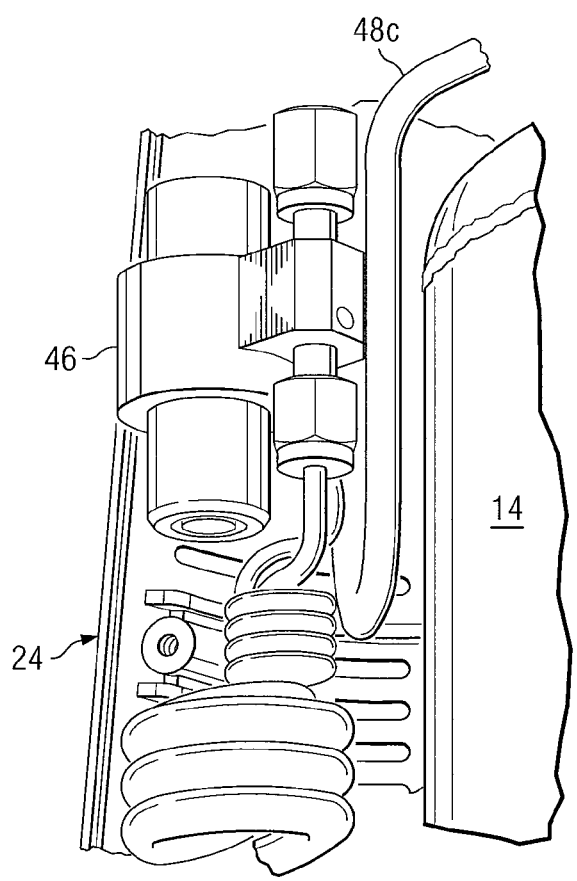
FIG. 14 illustrates an example relief/economizer valve physically decoupled from a container in accordance with one embodiment of the disclosure.

FIG. 13 illustrates vent valve 22 physically decoupled from container 14 in accordance with one embodiment of the disclosure. In this embodiment, vent valve support members 33 secure vent valve 22 physically separate from container 14, and vent valve 22 is connected to container 14 by tubing 48b. Tubing 48b may be coupled to an inlet 132 of vent valve 22 and to container 14 in any suitable manner, such as by weld, braze, or mechanical fastener. For example, in this embodiment, inlet 132 may be threaded to receive a ferrule nut 133 for securing tubing 48b to inlet 132. Such configuration may reduce the complexity and/or number of parts needed to connect inlet 132 to container 14.

The shape and/or configuration of tubing 48b may provide some flexibility and/or dampening such that the transfer of stresses or strains from vent valve 22 to container 14 may be reduced or substantially eliminated, as compared to a configuration in which vent valve 22 is directly coupled to container 14. Thus, for example, stresses and strains experienced by vent valve 22 due to actuation of vent valve lever 49 (e.g., during filling or otherwise) may not be transferred to container 14, as compared to a configuration in which vent valve 22 is directly coupled to container 14.

Also, in some embodiments, no flange is needed to mechanically connect vent valve 22 to container 14. The elimination of a flange may reduce the number of parts required for vent valve 22, the possibility of a leak or freezing, and/or the likelihood of container 14 being punctured (e.g., during filling or otherwise).

In addition, by physically decoupling vent valve 22 from container 14, heat generated by various high-temperature coupling techniques (e.g., welds or brazes) may be localized, which may reduce the likelihood of heat-sensitive components being damaged during such high-temperature coupling techniques. For example, in some embodiments, vent valve 22 may include one or more seals or other heat-sensitive components that may be damaged by exposure to high-temperatures. In such embodiments, high-temperature coupling techniques may be performed to couple tubing 48b to container 14 without damaging such heat-sensitive components due to the fact that such heat-sensitive components are physically displaced from container 14.

FIG. 14 illustrates relief/economizer valve 46 physically decoupled from container 14 in accordance with one embodiment of the disclosure. In this embodiment, relief/economizer valve support members 35 may secure relief/economizer valve 46 physically separate from container 14, and relief/economizer valve 46 may be connected to container 14 by tubing 48c. Tubing 48c may be coupled to relief/economizer valve 46 and container 14 in any suitable manner, such as by weld, braze, or mechanical fastener. The shape and/or configuration of tubing 48c may provide some flexibility and/or dampening such that the transfer of stresses or strains from relief/economizer valve 46 to container 14 may be reduced or substantially eliminated, as compared to a configuration in which relief/economizer valve 46 is directly coupled to container 14.

Figure 15A:
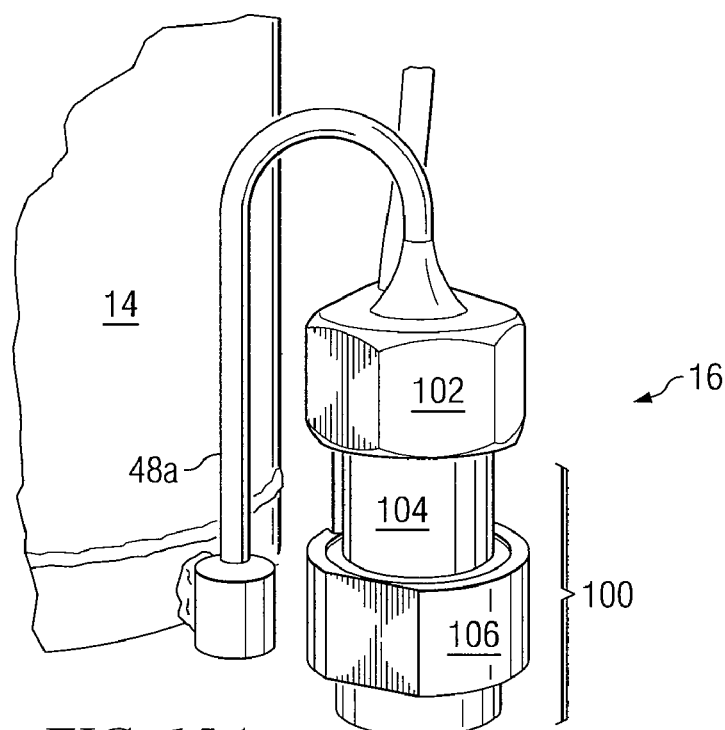
FIGS. 15A and 15B illustrates an example fill port according to one embodiment of the present disclosure.
Figure 15B:
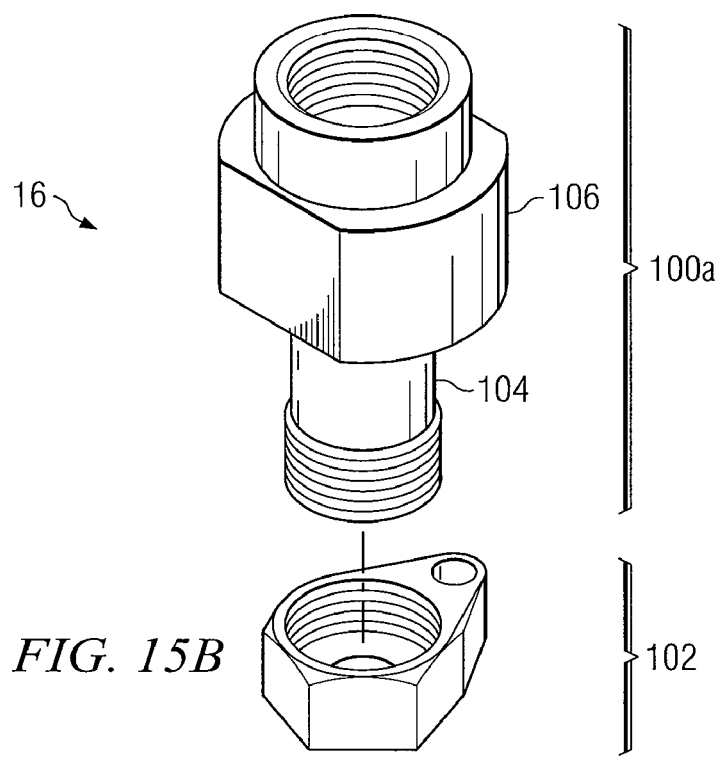
Figure 16:
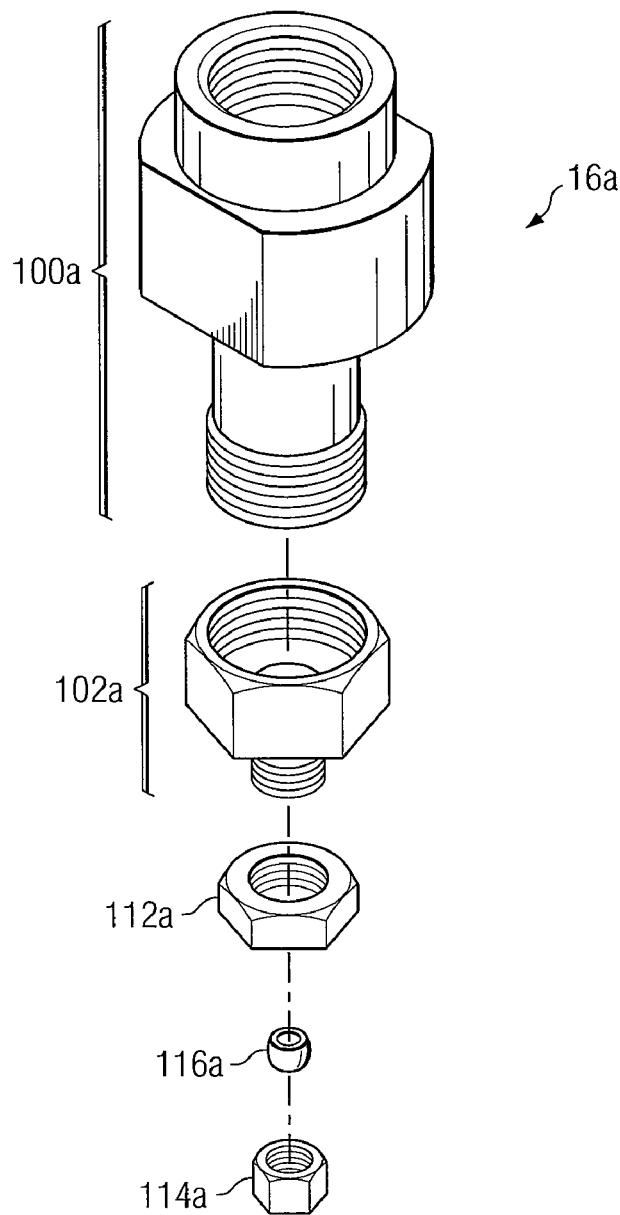
FIG. 16 illustrates an example prior art fill port.

FIGS. 15A and 15B illustrate an example fill port 16 according to one embodiment of the present disclosure. Fill port 16 may include a female fill connector assembly 100, and an adapter 102. Female fill connector assembly 100 may include a body portion 104 and a female sleeve connector portion 106. As discussed above, fill port 16 may be physically decoupled from container 14. For example, as shown in FIG. 12, adapter 102 may be coupled to container 14 via tubing 48a. Tubing 48a may be coupled to adapter 102 in any suitable manner, such as by welding, brazing, or using a mechanical fastener, for example. In contrast to certain prior art LOS apparatuses, fill port 16 of apparatus 10 may be secured by support members 30 rather than being coupled to container 14 by a flange or mechanical fastener. An example prior art fill port 16a is shown in FIG. 16. The prior art fill port 16a may include a female fill connector assembly 100a, an adaptor 102a, and one or more connection components and/or fasteners for connecting fill port 16a directly to the LOX container. For example, as shown in FIG. 16, such connection components and/or fasteners may include jam nut 112a, a ferrule nut 114a, and a compression sleeve 116a.

Thus, in embodiments of the present disclosure in which fill port 16 is not connected to container 14 via a flange, fill port 16 may not require such connection components and/or fasteners, such as jam nut 112a, ferrule nut 114a, compression sleeve 116a, and/or other fastener(s) to attach fill port 16 to such flange. Thus, fill port 16 may include fewer parts than prior fill ports, which may reduce the complexity and/or weight of LOX apparatus 10. In addition, the elimination of such connection components and/or fasteners (e.g., jam nut 112a, ferrule nut 114a, and/or compression sleeve 116a) to attach fill port 16 to a flange may remove another potential source of leakage and/or freezing.

Figure 17:
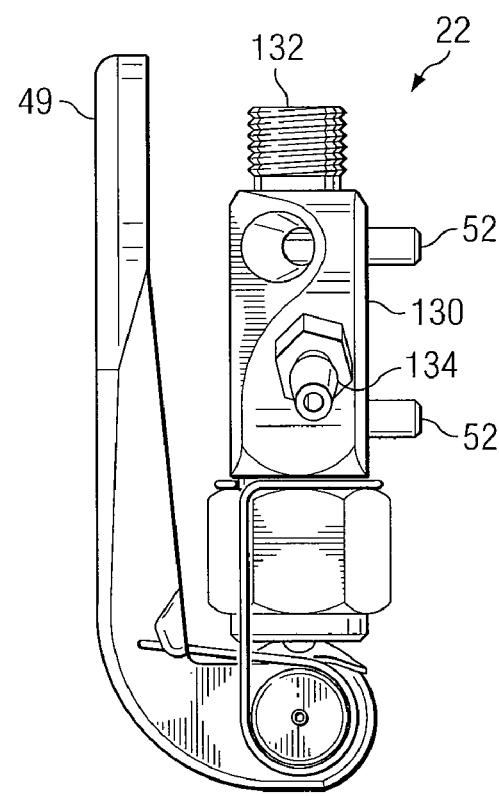
FIG. 17 illustrates a side view of an example vent valve in a closed valve position, according to one embodiment of the present disclosure.
Figure 18:
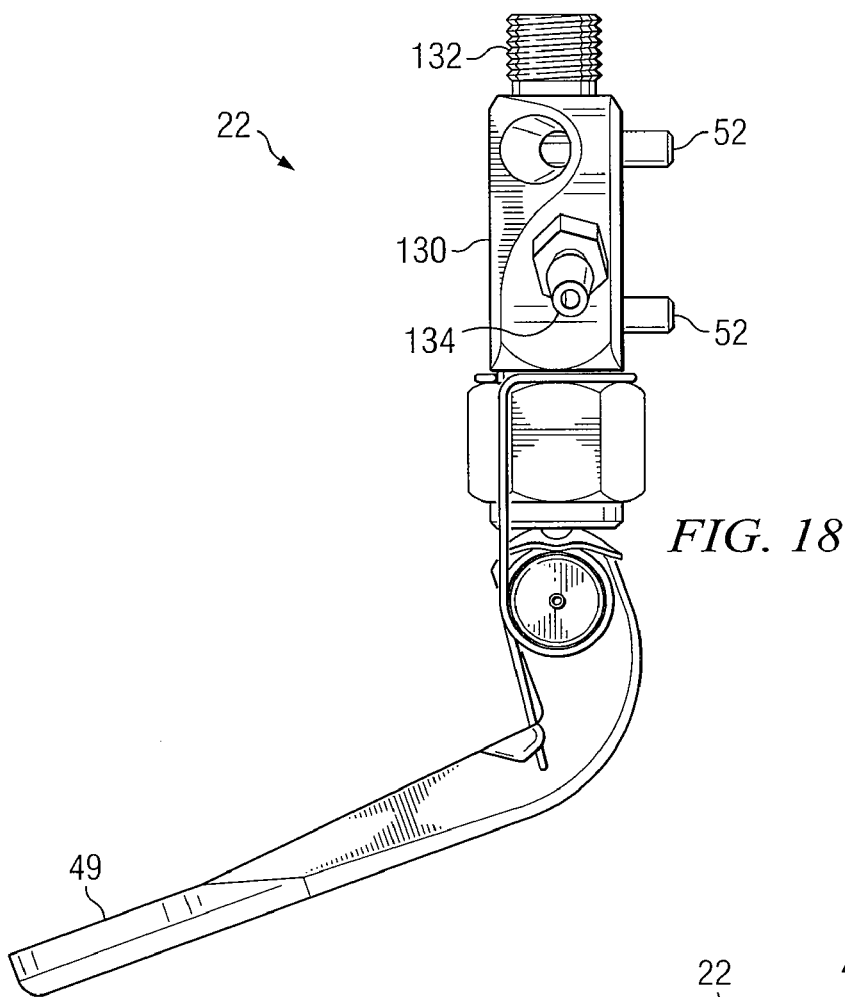
FIG. 18 illustrates a side view of an example vent valve in an open valve position, according to one embodiment of the present disclosure.
Figure 19:
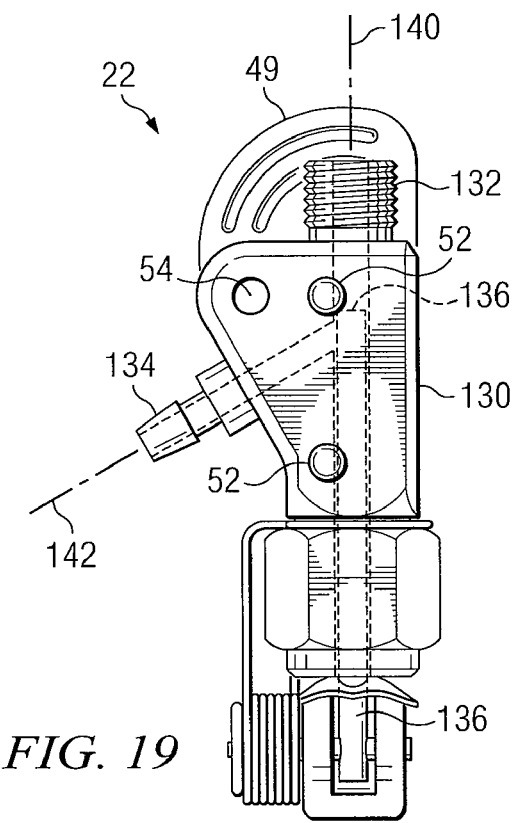
FIG. 19 illustrates a rear view of an example vent valve in a closed valve position, according to one embodiment of the present disclosure.
Figure 20:
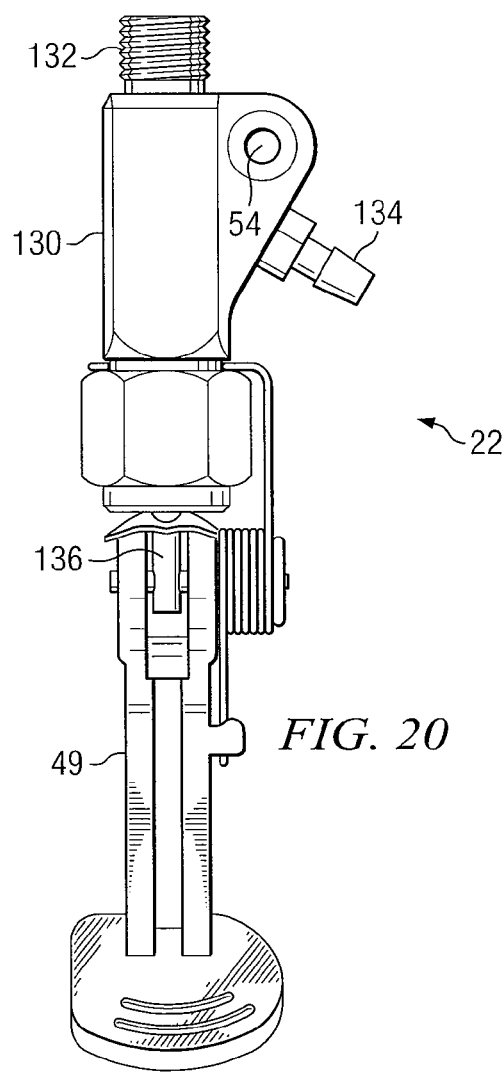
FIG. 20 illustrates a front view of an example vent valve in an open valve position, according to one embodiment of the present disclosure.

FIGS. 17-20 illustrate an example vent valve 22 in accordance with one embodiment of the present disclosure. In particular, FIG. 17 illustrates a side view of vent valve 22 in a closed valve position; FIG. 18 illustrates a side view of vent valve 22 in an open valve position; FIG. 19 illustrates a rear view of vent valve 22 in a closed position; and FIG. 20 illustrates a front view of vent valve 22 in an position.

Vent valve 22 may include a valve body 130, an inlet 132, an outlet 134, a valve lever 49, and/or a plunger 136 (see FIG. 20). In general, inlet 132 and outlet 134 may be connected by a passageway that may be closed (or blocked) or opened (or at least partially unblocked) based on the positioning of plunger 136 within an opening formed within valve body 130. Plunger 136 may be coupled to valve lever 49 such that actuation of valve lever 49 (e.g., manual actuation by a user) may pull plunger 136 downward from a closed position (see FIGS. 17 and 19) in which the passageway connecting inlet 132 and outlet 134 is closed to an open position (see FIGS. 18 and 20) in which the passageway connecting inlet 132 and outlet 134 is opened. Plunger 136 may include one or more sealing members configured to provide a suitable seal within valve body 130.

In some embodiments, valve body 130 may comprise a single integrated piece. This may be advantageous as compared to prior art valve bodies having multiple pieces joined together, as the joints between such multiple pieces may provide a potential source of leakage and/or freezing. In addition, in some embodiments, using a single-piece, integrated valve body 130 may eliminate the need for a seal or seals (such as an O-ring, for example) which may be included in prior valve bodies having multiple pieces. Thus, another source of leakage and/or freezing may be eliminated. In addition, vent valve 22 may include fewer parts than vent valves, which may reduce the complexity and/or weight of LOX apparatus 10.

In addition, one or both of inlet 132 and outlet 134 may be integral with valve body 130. In this example embodiment, inlet 132 is integral with valve body 130, whereas outlet 134 is separate and coupled to valve body 130. In other embodiments, valve body 130 may be formed from multiple pieces and/or both inlet 132 and outlet 134 may be separately coupled to valve body 130. As discussed above, valve body 130 may include one or more alignment pegs 52 used for aligning and/or securing vent valve 22 relative to housing 12.

In some embodiments, inlet 132 and outlet 134 may be formed in the same general plane or in generally parallel planes. For example, an axis 140 defined by inlet 132 and an axis 142 defined by outlet 134 may reside in the same or generally parallel planes. This may provide various advantages, such as increased ease of manufacturing and/or assembly, which may improve product quality and/or reliability. In addition, configuring vent valve 22 as described herein and/or the use of support members 33 may reduce or eliminate the likelihood of vent valve 22 being misaligned during assembly or otherwise, which may also improve product quality and/or reliability.

As discussed above, fill port 16 may be physically decoupled from container 14. For example, as shown in FIG. 13, inlet 132 may be configured to be coupled to container 14 by tubing 48b, rather than being directly coupled to container 14. The shape and configuration of tubing 48b may provide some flexibility and/or dampening such that the transfer of stresses or strains from vent valve 22 to container 14 may be reduced or substantially eliminated, as compared to a configuration in which vent valve 22 is directly coupled to container 14. Tubing 48b may be coupled to inlet 132 in any suitable manner, such as by weld, braze, or mechanical fastener. For example, in this embodiment, inlet 132 may be threaded to receive a ferrule nut to secure tubing 48b to inlet 132. Such configuration may reduce the complexity and/or number of parts needed to connect inlet 132 to container 14.

Figure 21:
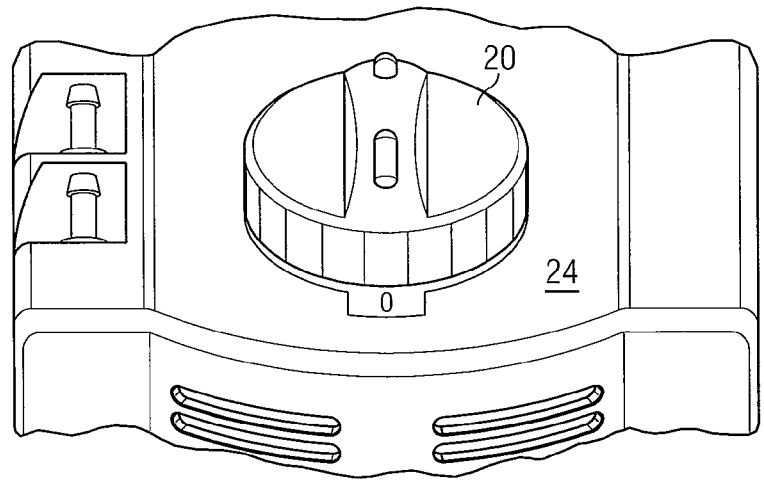
FIG. 21 illustrates an example control device of an LOX apparatus positioned in an off position, according to one embodiment of the present disclosure.
Figure 22:
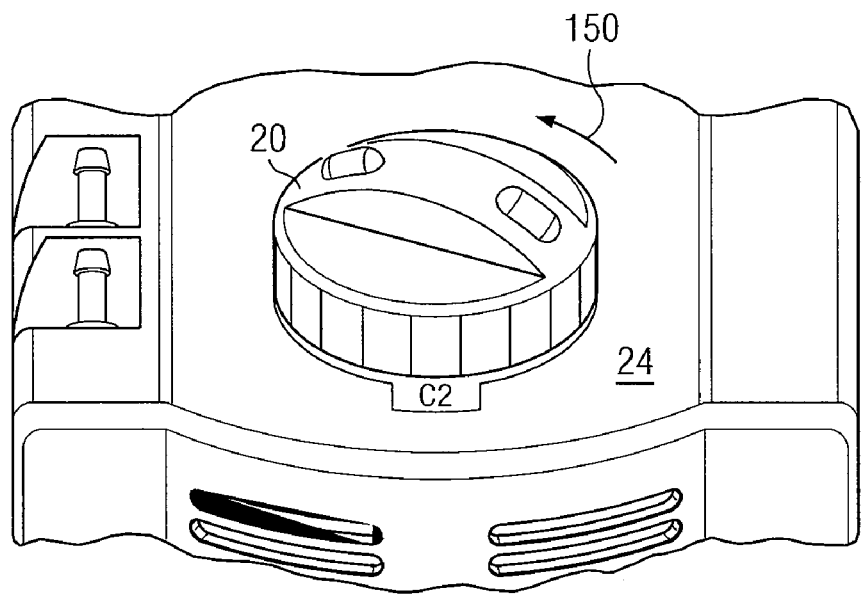
FIG. 22 illustrates an example control device of an LOX apparatus positioned in a continuous mode position, according to one embodiment of the present disclosure.
Figure 23:
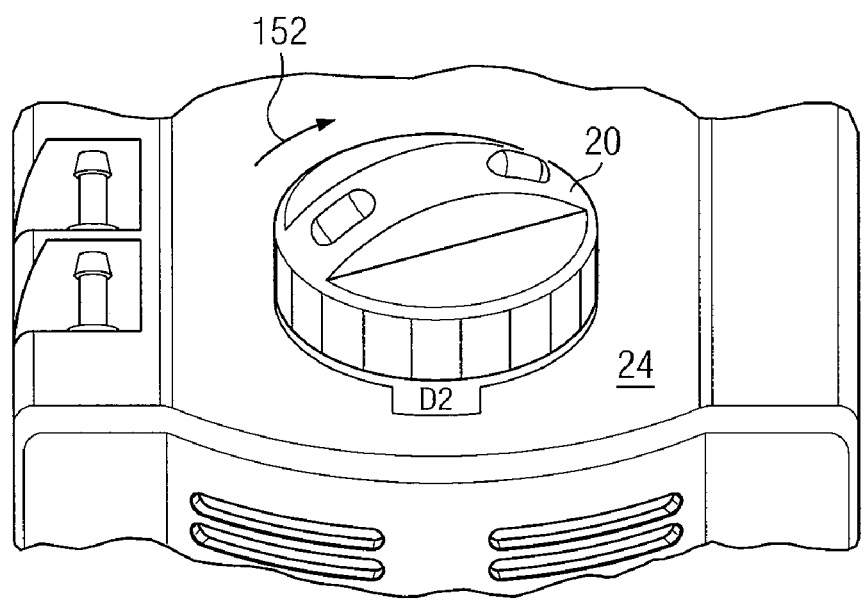
FIG. 23 illustrates an example control device of an LOX apparatus positioned in a conserve mode position, according to one embodiment of the present disclosure.

FIGS. 21-23 illustrate an example control device 20 for adjusting or controlling the flow of gaseous oxygen delivered by apparatus 10, according to one embodiment of the disclosure. As discussed above, control device 20 may be configured to be manipulated by a user to adjust or control the flow of gaseous oxygen delivered by apparatus 10. In this example, control device 20 comprises a single knob that allows a user to (a) select between at least three modes of operation: off, continuous mode, and conserve (or demand) mode, and (b) select the intensity, flow rate, level, or flow type for the selected mode. The various modes of operation and intensities (or flow rates) may be regulated by regulator 44, such as discussed above with respect to FIG. 2.

In the embodiment shown in FIGS. 21-23, control device 20 comprises a single knob that may be rotated to select any of the following settings, each indicated on the knob using the following labels:

| Knob label | Mode and/or intensity/flow rate/level |
|---|---|
| O | Off |
| $C_1$ | Continuous mode, flow rate #1 |
| $C_2$ | Continuous mode, flow rate #2 |
| $C_3$ | Continuous mode, flow rate #3 |
| $C_4$ | Continuous mode, flow rate #4 |
| $C_5$ | Continuous mode, flow rate #5 |
| $C_6$ | Continuous mode, flow rate #6 |
| $D_{1.5}$ | Conserve mode #1 |
| $D_2$ | Conserve mode #2 |
| $D_{2.5}$ | Conserve mode #3 |
| $D_3$ | Conserve mode #4 |
| $D_4$ | Conserve mode #5 |

Thus, the user may easily—e.g., using a single knob—select between multiple modes and or intensities or flow rates as desired, which may be advantageous over apparatuses in which the user must manipulate multiple control devices to select such options.

FIG. 21 illustrates knob 20 positioned in the off position (labeled "O"). FIG. 22 illustrates knob 20 positioned in a particular continuous mode position (labeled "$C_2$"), after being rotated counter-clockwise from the off position, as indicated by arrow 150. FIG. 23 illustrates knob 20 positioned in a particular continuous mode position (labeled "$D_2$"), after being rotated clockwise from the off position, as indicated by arrow 152.

Although the disclosed embodiments have been described in detail, it should be understood that various changes, substitutions and alterations can be made herein without departing from the spirit and scope of the disclosure as illustrated by the following claims. For example, it should be understood that in various embodiments, apparatus 10 may include any combination of one, some or all of the various components and/or features discussed above and/or any one or more additional components and/or features.

What is claimed is:

1. A fluid storage and delivery apparatus, comprising:
   a fluid container;
   a vent valve; and
   a housing including a first housing portion and a second housing portion, the first housing portion including one or more vent valve support ribs for supporting the vent valve;
   wherein the second housing portion defines a vent valve opening; and
   wherein a first portion of the vent valve is secured physically separate from the fluid container by the one or more vent valve support ribs and a second portion of the vent valve extends through the vent valve opening when the first and second housing portions are assembled together.

2. An apparatus according to claim 1, wherein the fluid container is configured for storing liquid oxygen and delivering gaseous oxygen.

3. An apparatus according to claim 1, further comprising:
   a fill port for filling the fluid container;
   the first housing portion further including one or more fill port support ribs for supporting the fill port;
   wherein assembling the first and second housing portions together defines a fill port opening; and
   wherein a first portion of the fill port is secured physically separate from the fluid container by the one or more fill port support ribs and a second portion of the fill port extends through the fill port opening defined by the assembled first and second housing portions.

4. An apparatus according to claim 3, wherein:
   the fill port includes a first portion having a first shape and a second portion having a second shape different from the first shape; and
   the one or more fill port support ribs comprise at least one first rib shaped to receive the first portion of the fill port and at least one second rib shaped to receive the second portion of the fill port.

5. An apparatus according to claim 1, further comprising:
   an economizer valve for regulating the pressure of fluid within fluid container; and
   one or more economizer valve support ribs coupled to the first housing portion for supporting the economizer valve.

6. An apparatus according to claim 1, wherein the first housing portion further includes support ribs configured to secure a fill port and an economizer valve physically separate from the fluid container.

7. An apparatus according to claim 1, wherein at least one of the vent valve support ribs is formed integrally with the housing.

8. An apparatus according to claim 1, wherein at least one of the vent valve support ribs is shaped to match a contour of the vent valve.

9. An apparatus according to claim 1, further comprising one or more coupling members at least partially defining a fluid passageway between the vent valve and the fluid container, wherein the one or more coupling members are flexible to provide dampening between the vent valve and the fluid container.

10. An apparatus according to claim 1, wherein the second housing portion includes one or more second vent valve support ribs configured to cooperate with one or more first vent valve support ribs to secure the vent valve physically separate from the fluid container.

11. An apparatus according to claim 1, wherein:
   the second housing portion includes one or more vent valve support ribs for supporting the vent valve; and
   wherein the first portion of the vent valve is secured physically separate from the fluid container by the one or more vent valve support ribs of the first housing portion and by the one or more vent valve support ribs of the second housing portion.

12. A housing for a fluid storage and delivery apparatus, comprising:

a first housing portion and a second housing portion configured, when assembled together, to at least partially house multiple components of the fluid storage and delivery apparatus;

one or more first support ribs coupled to the first housing portion; and one or more second support ribs coupled to the second housing portion;

wherein assembling the first housing portion with the second housing portion defines an opening between the first and second housing portions, wherein a first one of the components extends through the opening; and wherein the one or more first support ribs cooperate with the one or more second support ribs to secure the first component physically separate from a second one of the components, the first and second components being indirectly coupled to each other by one or more coupling members at least partially defining a fluid passageway between the first and second components.

13. A housing according to claim 12, wherein the fluid storage and delivery apparatus comprises a liquid oxygen storage and delivery apparatus for storing liquid oxygen and delivering gaseous oxygen.

14. A housing according to claim 12, wherein:
the second component comprises a container for storing a pressurized liquid;
the first component comprises a fill port for filling the container; and
the one or more coupling members comprise tubing for communicating liquid from the fill port into the container.

15. A housing according to claim 14, wherein:
the fill port includes a first portion having a first shape and a second portion having a second shape different from the first shape; and
the one or more first support ribs comprise a first portion shaped to receive the first portion of the fill port and a second portion shaped to receive the second portion of the fill port.

16. A housing according to claim 12, wherein the one or more support members are configured to secure a fill port, a vent valve, and an economizer valve physically separate from a fluid container.

17. A housing according to claim 12, wherein at least one of the first support ribs is formed integrally with the first housing portion, and at least one of the second support ribs is formed integrally with the second housing portion.

18. A housing according to claim 12, wherein at least one of the first support ribs is shaped to match a contour of the first component.

19. A housing according to claim 12, wherein the one or more coupling members are flexible to provide dampening between the first component and the second component.

20. A fluid storage and delivery apparatus, comprising:

means for storing a fluid;

means for communicating at least a portion of the fluid to or from the fluid storage means; and means for at least partially housing the fluid storage means and the fluid communication means, including a first housing means portion and a second housing means portion, the first housing means portion including one or more support ribs for supporting the fluid communication means;

wherein assembling the first and second housing means portions together defines an opening; and wherein a first portion of the fluid communication means is secured physically separate from the fluid storage means at least by the one or more support ribs and a second portion of the fluid communication means extends through the opening defined by the assembled first and second housing means portions.

21. An apparatus according to claim 20, wherein the fluid communication means comprises a fill port.

* * * * *